(12) United States Patent
Sung

(10) Patent No.: US 7,390,506 B2
(45) Date of Patent: *Jun. 24, 2008

(54) LIPOPHILIC DRUG COMPOSITIONS

(76) Inventor: Michael T. Sung, 1604 Reston Ct., Raleigh, NC (US) 27614

( * ) Notice: Subject to any disclaimer, the term of this patent is extended or adjusted under 35 U.S.C. 154(b) by 0 days.

This patent is subject to a terminal disclaimer.

(21) Appl. No.: 11/367,929

(22) Filed: Mar. 3, 2006

(65) Prior Publication Data

US 2006/0147525 A1      Jul. 6, 2006

Related U.S. Application Data

(63) Continuation of application No. 10/134,329, filed on Apr. 29, 2002, now Pat. No. 7,125,568.

(60) Provisional application No. 60/314,092, filed on Aug. 23, 2001.

(51) Int. Cl.
  A61K 9/16    (2006.01)
  A61K 9/56    (2006.01)
  A61K 31/41   (2006.01)
(52) U.S. Cl. .................... 424/498; 424/484; 424/489; 424/439; 514/359; 514/365; 514/385
(58) Field of Classification Search .............. None
See application file for complete search history.

(56) References Cited

U.S. PATENT DOCUMENTS

| 3,931,213 A | 1/1976 | Kaminski et al. |
|---|---|---|
| 3,950,351 A | 4/1976 | Rossignol et al. |
| 4,186,129 A | 1/1980 | Huth et al. |
| 4,315,018 A | 2/1982 | Rossignol |
| 4,877,561 A | 10/1989 | Iga et al. |
| 4,895,719 A | 1/1990 | Radhakrishnan et al. |
| 5,043,165 A | 8/1991 | Radhakrishnan |
| 5,340,587 A | 8/1994 | Mihalko et al. |
| 5,512,671 A | 4/1996 | Piantadosi et al. |
| 5,534,499 A | 7/1996 | Ansell |
| 5,565,571 A | 10/1996 | Barbachyn et al. |
| 5,576,016 A | 11/1996 | Amselem et al. |
| 5,599,831 A | 2/1997 | Poretz et al. |
| 5,643,907 A | 7/1997 | Swirska et al. |

(Continued)

FOREIGN PATENT DOCUMENTS

EP    0 316 594 A1    5/1989

(Continued)

OTHER PUBLICATIONS

Gillard, J. et al., "The Release of Quinidine Sulphate from Inert, Hydrophilic and Lipophilic Matrices," *Sciences Techniques et Pratiques Pharmaceutiques*, 1987, pp. 492-500, vol. 3(6).

(Continued)

*Primary Examiner*—Gollamudi S. Kishore
(74) *Attorney, Agent, or Firm*—Alston & Bird LLP

(57) ABSTRACT

The invention is directed to biologically active lipophilic compositions comprising a biologically active covalently attached to, or encapsulated within, a lipid. Preferably, a biologically active agent is both covalently attached to a lipid and encapsulated within a lipid composition. Preferred lipid components include triglycerides and fatty acids. The resulting composition is preferably adapted for oral administration.

32 Claims, 7 Drawing Sheets

U.S. PATENT DOCUMENTS

| | | |
|---|---|---|
| 5,662,932 A | 9/1997 | Amselem et al. |
| 5,668,286 A | 9/1997 | Yamada et al. |
| 5,688,525 A | 11/1997 | Adler-Moore et al. |
| 5,688,792 A | 11/1997 | Barbachyn et al. |
| 5,700,777 A | 12/1997 | Sarin et al. |
| 5,700,799 A | 12/1997 | Hutchinson et al. |
| 5,716,637 A | 2/1998 | Anselem et al. |
| 5,719,154 A | 2/1998 | Tucker et al. |
| 5,795,589 A | 8/1998 | Mayer et al. |
| 5,798,348 A | 8/1998 | Alemany |
| 5,817,334 A | 10/1998 | Schmidt et al. |
| 5,856,348 A | 1/1999 | Rossignol |
| 5,859,038 A | 1/1999 | Rossignol |
| 5,874,111 A | 2/1999 | Maitra et al. |
| 5,886,013 A | 3/1999 | Rossignol |
| 5,935,591 A | 8/1999 | Rossignol et al. |
| 5,936,092 A | 8/1999 | Shen et al. |
| 5,939,096 A | 8/1999 | Clerc et al. |
| 5,962,437 A | 10/1999 | Kucera et al. |
| 5,965,590 A | 10/1999 | Rossignol |
| 5,968,961 A | 10/1999 | Rossignol |
| 5,989,583 A | 11/1999 | Amselem |
| 6,011,020 A | 1/2000 | Gold et al. |
| 6,020,353 A | 2/2000 | Rossignol |
| 6,060,080 A | 5/2000 | Kikuchi et al. |
| 6,071,532 A | 6/2000 | Chaikof et al. |
| 6,080,725 A | 6/2000 | Marciani |
| 6,117,894 A | 9/2000 | Rossignol |
| 6,120,751 A | 9/2000 | Unger |
| 6,147,204 A | 11/2000 | Gold et al. |
| 6,153,119 A | 11/2000 | Sung |
| 6,166,056 A | 12/2000 | Thomas et al. |
| 6,168,778 B1 | 1/2001 | Janjic et al. |
| 6,180,136 B1 | 1/2001 | Larson et al. |
| 6,225,445 B1 | 5/2001 | Shen et al. |
| 6,241,999 B1 | 6/2001 | Ye et al. |
| 6,287,591 B1 | 9/2001 | Semple et al. |
| 6,288,238 B1 | 9/2001 | Hollingsworth et al. |
| 6,337,329 B1 | 1/2002 | Cochran et al. |
| 2001/0056116 A1 | 12/2001 | Shashoua |
| 2002/0177609 A1 | 11/2002 | Swindell et al. |
| 2003/0023104 A1 | 1/2003 | Whittaker et al. |

FOREIGN PATENT DOCUMENTS

| | | |
|---|---|---|
| WO | WO 96/22303 A1 | 7/1996 |
| WO | WO 00/59482 A1 | 10/2000 |
| WO | WO 01/45744 A2 | 6/2001 |

OTHER PUBLICATIONS

Vatistas, "Initial Experiences With the Use of Nitazoxanide in the Treatment of Equine Protozoal Encephalitis in Northern California", *Equine Practice*, May 1999, 18-21, vol. 21, No. 5.

SYNTHESIS OF NITROTHIAZOLYL-LAURAMIDE

UV SPECTRA OF BA 3540

LIPOPHILIC DRUG COMPOSITIONS

CROSS-REFERENCE TO RELATED APPLICATIONS

This application is a continuation of U.S. application Ser. No. 10/134,329, filed Apr. 29, 2002, now U.S. Pat. No. 7,125,568 which claims the benefit of Provisional Application Ser. No. 60/314,092, filed Aug. 23, 2001, both of which are incorporated herein by reference in their entirety.

FIELD OF THE INVENTION

The invention relates to lipophilic drug compositions comprising biologically active agents in association with lipid components, methods of making such compositions, and methods of using such compositions in drug delivery.

BACKGROUND OF THE INVENTION

The small intestine is the primary site for the absorption of drugs administered orally. The most important element in the small intestine controlling absorption is the brush border membrane. It consists of a phospholipid bilayer into which polysaccharides and proteins are incorporated. This membrane creates absorption barriers to many polar drugs. A successful approach in the pharmaceutical industry has been to synthesize prodrugs with increasing membrane permeability by esterifying the charge functionalities. For example, the prodrug of 6-azauridine for the treatment of psoriasis and neoplastic disease is acetylated to form 2',3',5'-triacetyl-6-azauridine in order to enhance bioavailability (Bloch, A., "The Design of Biologically Active Nucleoside", *Drug Design*, Vol. IV, Chapter 8, Ariens, E J (Ed.), Academic Press, New York, 1973) (see also, Sinkula, A A, "Application of the Prodrug Approach to Antibiotics", Pro-drug as Novel Drug Delivery Systems, pp 116-153, Higuchi, T. and Stella, V. (Eds.), ACS Symposium Series 14, American Cancer Society, Washington D.C., 1975; Yalkowski, S H and Morozowich, W., *Drug Design*, Vol.9, pp 121, Ariens, E J (Ed.), Academic Press, New York, 1980).

Pharmacokinetics measures the fate of drugs at the time of ingestion until elimination from the body. Bioavailability of a drug following an oral dosing is determined by its pharmacokinetics. At least three factors dictate the efficacy of a drug: 1) the degree of drug absorption through the GI tract; 2) the ease with which it becomes inactivated by the biotransformation mechanisms of the liver and 3) the rate of elimination from the body. The pharmaceutical industry usually focuses on drug formulation to increase drug efficacy by increasing drug absorption. Hence, in recent years, there has been an explosion of drug encapsulation technology. The basic premise of drug encapsulation is to improve drug delivery, lessen toxicity and improve efficacy.

The use of liposome technology as a drug delivery system has been a particularly active area of research. These lipid vesicles are generally neutral or zwitterionic lipids arranged into bilayers that entrap one (unilamellar) or more (multilamellar) spaces. In conventional liposomes, it is often difficult to entrap a high concentration of a drug. Further, in long-term storage, a drug entrapped within liposomes may leak. The cost of pharmaceutical grade phospholipids used in liposomes is also cost prohibitive. Thus, it is preferably for use in injectable formulations rather than for oral formulation (see M. Ostro, "Liposomes", Marcel Dekker, New York, 1983).

There remains a need in the art for cost-effective methods of improving drug efficacy and bioavailability and lessening drug toxicity.

SUMMARY OF THE INVENTION

The present invention provides biologically active lipophilic compositions, particularly solid compositions adapted for oral administration. The lipophilic compositions of the invention exhibit improved bioavailability and reduced toxicity as compared to non-lipophilic parent drug compounds. The invention involves covalently attaching a lipid molecule to a biologically active agent and/or encapsulating a biological active agent within a lipid composition. Preferably, the lipid molecule covalently attached to the biologically active agent is a non-amphipathic lipid, such as a triglyceride or a fatty acid. Similarly, the encapsulating lipid composition is preferably non-amphipathic. In a preferred embodiment, a biologically active agent is covalently attached to a C4-C30 fatty acid and then encapsulated within a mixture of at least one triglyceride and at least one fatty acid. The linkage between the biologically active agent and the lipid is preferably hydrolytically stable and enzymatically cleavable. Examples of suitable linkages include ethers, thioethers, imides, amides, sulfonamides, phosphonamides, disulfides, and carbamides.

The biologically active agent can be, for example, peptide, protein, enzyme, small molecule drug, dye, nucleoside, oligonucleotide, oligosaccharide, polysaccharide, vaccine, cell, or a virus. In one embodiment, the biologically active agent is the biologically active core structure of a known group of structurally similar compounds having a common biological activity, such as penicillins, floxins, ACE inhibitors, and the like. The biologically active core structure can be determined by analyzing the structurally similar compounds and selecting the structural components shared by the structurally similar compounds, the shared structural components forming the biologically active core structure.

The encapsulation of the biologically active agent can be readily accomplished by dissolving a first lipid composition (e.g., C4-C30 fatty acid) in a solvent, mixing the dissolved lipid with the biologically active agent with sufficient mixing intensity to form an emulsified mixture, adding a second lipid composition (e.g., one or more triglycerides) to the emulsified mixture while continuing to mix the emulsified mixture, solidifying the mixture, and drying the mixture to form a dry solid composition.

In another aspect, the present invention provides a biologically active lipophilic compound comprising a substituted or unsubstituted 5-nitrothiazole covalently attached to a lipid molecule, for example, having the structure:

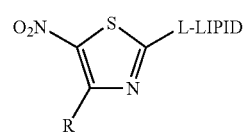

wherein L is a linkage, such as an amide linkage, R is hydrogen, alkyl, substituted alkyl, aryl, substituted aryl, heteroaryl, substituted heteroaryl, heterocyclic, or substituted heterocyclic, and LIPID is a residue of a C4-C30 fatty acid. The above-described 5-nitrothiazole derivative is useful for treating an infection in a mammal, such as a parasitic, bacterial, viral, or fungal infection.

BRIEF DESCRIPTION OF THE DRAWINGS

Figure 1:
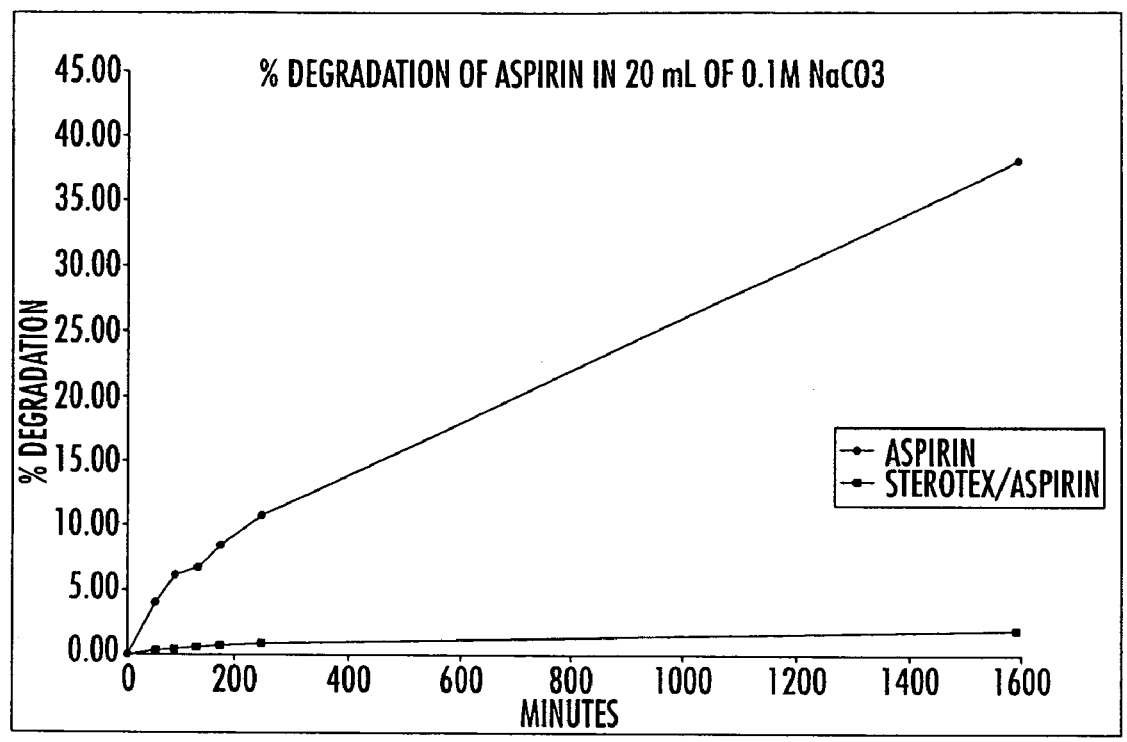
Figure 2:
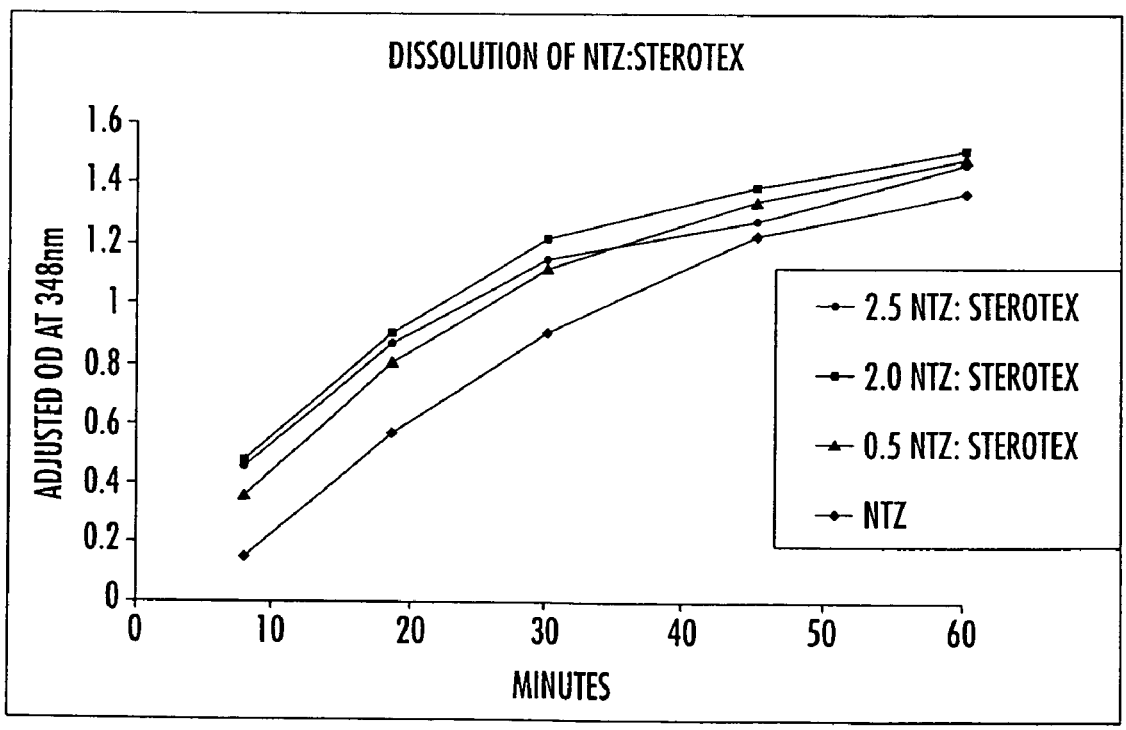
Figure 3:
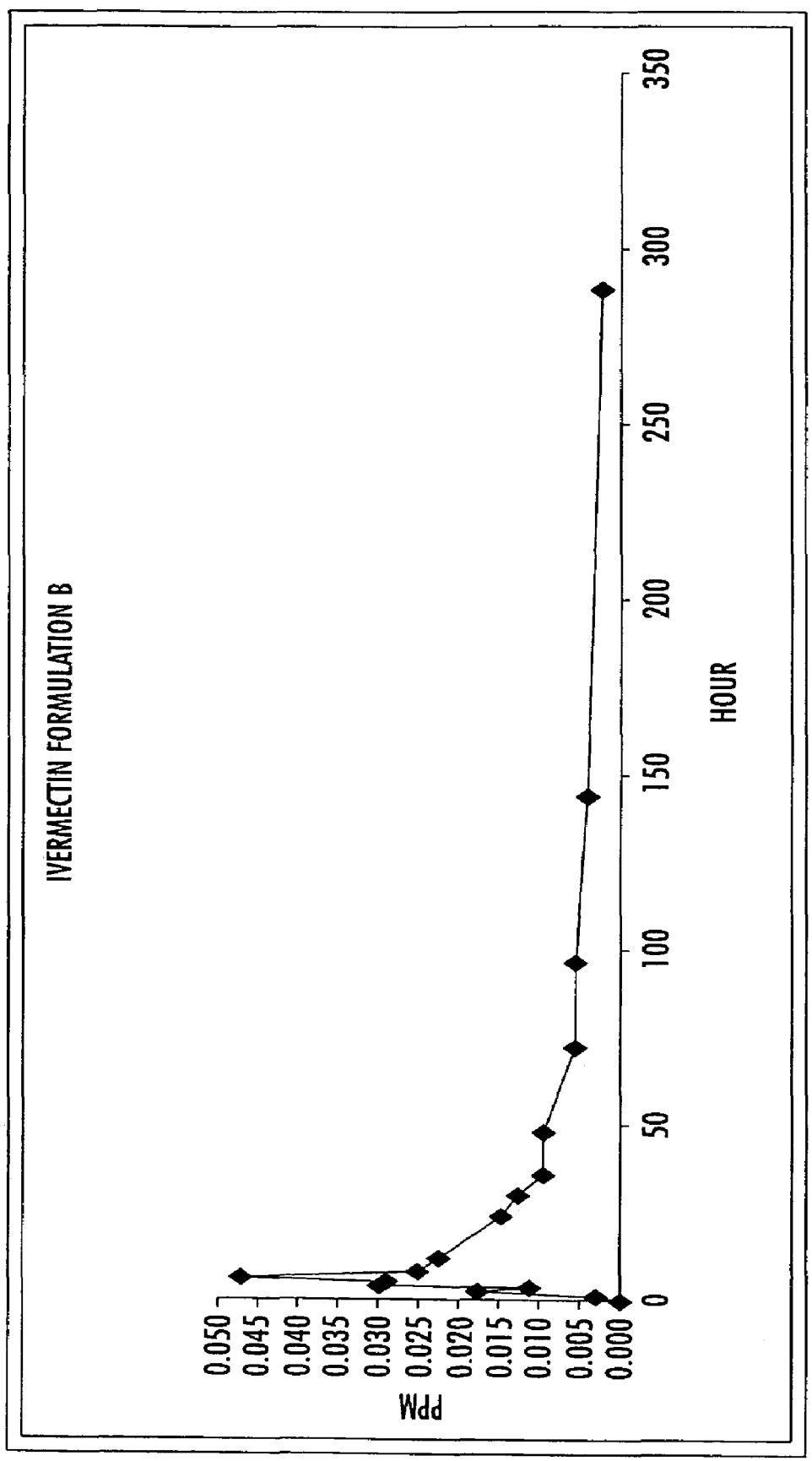
Figure 4:
Figure 5:
Figure 6:
Figure 7:
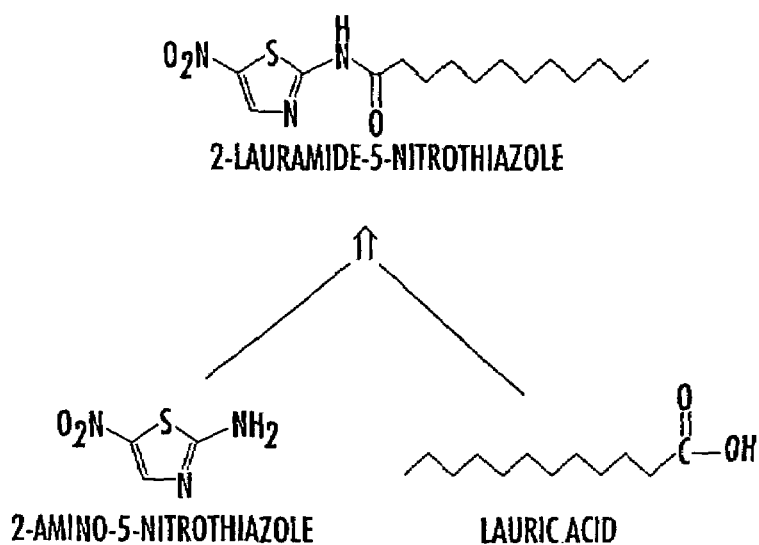
Figure 8:
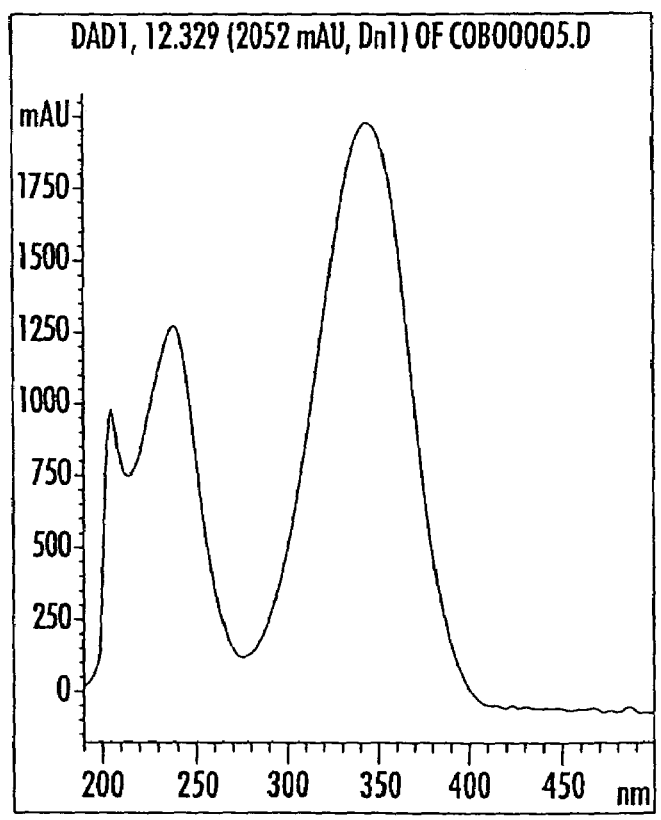
Figure 9:
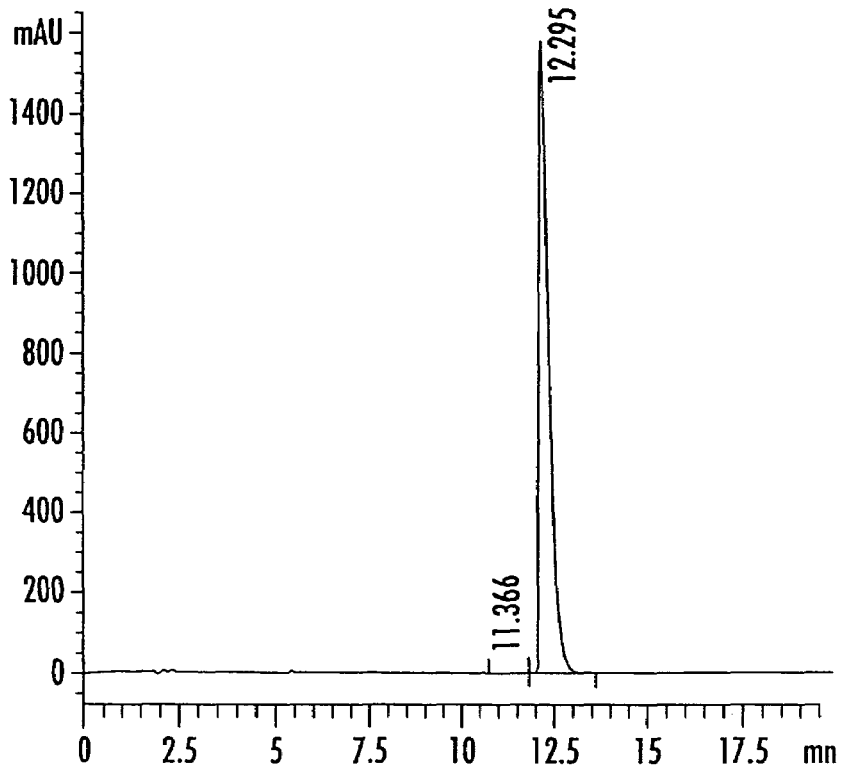

Having thus described the invention in general terms, reference will now be made to the accompanying figures, wherein:

FIG. 1 illustrates the rate of degradation of aspirin and encapsulated aspirin in sodium carbonate;

FIG. 2 illustrates the in-vitro bioavailability of NTZ and encapsulated NTZ when subjected to dissolution;

FIG. 3 illustrates the pharmacokinetic profile of ivermectin from a horse that was dosed with the Sterotex® encapsulated drug;

FIG. 4 is a freeze fracture electron micrograph taken at about 27K magnification of NTZ encapsulated in Sterotex®/palmatate;

FIG. 5 is a freeze fracture electron micrograph taken at 8.3K magnification of NTZ encapsulated in Sterotex®/palmatate;

FIG. 6 is a second freeze fracture electron micrograph taken at about 8.3 K magnification of NTZ encapsulated in Sterotex®/palmatate;

FIG. 7 illustrates a method of synthesis for compound BA 3540;

FIG. 8 is a graph of the UV spectra for compound BA 3540;

FIG. 9 is a graph of the HPLC data for compound BA 3540; and

Figure 10:
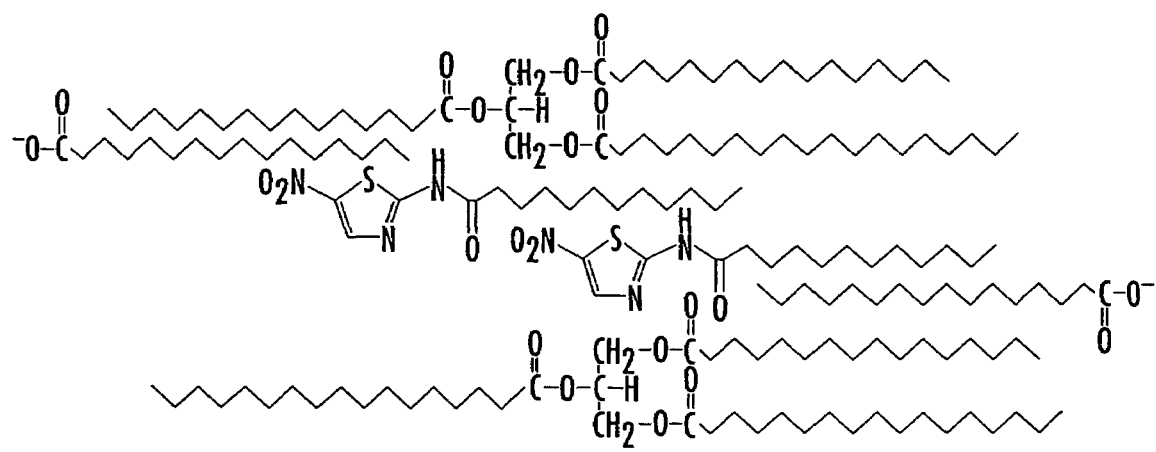

FIG. 10 illustrates the encapsulated compound BA 3540 coalescing with encapsulating fatty acid and triglyceride tails.

DETAILED DESCRIPTION OF THE INVENTION

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

I. Definitions

The terms "functional group", "active moiety", "activating group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules. The term "active," when used in conjunction with functional groups, is intended to include those functional groups that react readily with electrophilic or nucleophilic groups on other molecules, in contrast to those groups that require strong catalysts or highly impractical reaction conditions in order to react (i.e., "non-reactive" or "inert" groups). For example, as would be understood in the art, the term "active ester" would include those esters that react readily with nucleophilic groups such as amines. Exemplary active esters include N-hydroxysuccinimidyl esters or 1-benzotriazolyl esters. Typically, an active ester will react with an amine in aqueous medium in a matter of minutes, whereas certain esters, such as methyl or ethyl esters, require a strong catalyst in order to react with a nucleophilic group.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pHs, e.g., under physiological conditions for an extended period of time, perhaps even indefinitely. Hydrolytically unstable or degradable linkages means that the linkages are degradable in water or in aqueous solutions, including for example, blood. Enzymatically unstable, degradable or cleavable linkages means that the linkage can be degraded by one or more enzymes.

The term "alkyl" refers to hydrocarbon chains typically ranging from about 1 to about 24 carbon atoms in length, and includes straight and branched chains. The hydrocarbon chains may be saturated or unsaturated. The term "substituted alkyl" refers to an alkyl group substituted with one or more non-interfering substituents, such as, but not limited to, C3-C6 cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino and dialkylamino, e.g., methylamino; ketone; halo, e.g. chloro or bromo; phenyl; substituted phenyl, and the like.

"Alkoxy" refers to an —O—R group, wherein R is alkyl or substituted alkyl, preferably C1-C6 alkyl (e.g., methoxy or ethoxy).

"Aryl" means one or more aromatic rings, each of 5 or 6 core carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents. For substitutions on a phenyl ring, the substituents may be in any orientation (i.e., ortho, meta or para).

"Heteroaryl" is an aryl group containing from one to four N, O, or S atoms(s) or a combination thereof, which heteroaryl group is optionally substituted at carbon or nitrogen atom(s) with C1-6 alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms.

"Substituted heteroaryl" is heteroaryl having one or more non--interfering groups as substituents.

"Heterocycle" or "heterocyclic" means one or more rings of 5, 6 or 7 atoms with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents" are those groups that yield stable compounds. Suitable non-interfering substituents or radicals include, but are not limited to, halo, C1-C10 alkyl, C2-C10 alkenyl, C2-C10 alkynyl, C1-C10 alkoxy, C7-C12 aralkyl, C7-C12 alkaryl, C3-C10 cycloalkyl, C3-C10 cycloalkenyl, phenyl, substituted phenyl, toluoyl, xylenyl, biphenyl, C2-C12 alkoxyalkyl, C7-C12 alkoxyaryl, C7-C12 aryloxyalkyl, C6-C12 oxyaryl, C1-C6 alkylsulfinyl, C1-C10 alkylsulfonyl, —(CH$_2$)$_m$—O—(C1-C10 alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C1-C10 alkyl), —C(O)—(C1-C10 alkyl), C2-C10 thioalkyl, —C(O)O—(C1-C10 alkyl), —OH, —SO$_2$, =S, —COOH, —NR, carbonyl, —C(O)—(C1-C10 alkyl)-CF$_3$, —C(O)—CF$_3$, —C(O)NR$_2$, —(C1-C10 alkyl)-S—(C6-C12 aryl), —C(O)—(C6-C12 aryl), —(CH$_2$)$_m$—O—(CH$_2$)$_m$—O—(C1-C10 alkyl) wherein each m is from 1 to 8, —C(O)NR, —C(S)NR, —SO$_2$NR, —NRC(O)NR, —NRC(S)NR, salts thereof, and the like. Each R as used herein is H, alkyl or substituted alkyl, aryl or substituted aryl, aralkyl, or alkaryl.

The term "drug", "biologically active molecule", "biologically active moiety" or "biologically active agent", when used herein means any substance which can affect any physical or biochemical properties of a biological organism, including but not limited to, viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, nucleosides, oligonucleotides, oligosaccharides, polysaccharides, vaccines, cells, or viruses. Classes of biologically active agents that are suitable for use with the invention include, but are not limited to, parasiticides, antibiotics, fungicides, anti-viral agents, anti-inflammatory agents, anti-tumor agents, cardiovascular agents, anti-anxiety agents, hormones, growth factors, steroidal agents, and the like. In some preferred embodiments, the drug or biologically active moiety is a small drug molecule having a molecular weight of less than about 800 Da.

"Lipophilic" or hydrophobic refers to molecules having a greater solubility in octanol than in water, typically having a much greater solubility in octanol. Conversely, "hydrophilic" refers to molecules having a greater solubility in water than in octanol.

"Lipid" encompasses oils, fats and fat-like substances that occur in living organisms and that characteristically are soluble in relatively nonpolar organic solvents (e.g. benzene, chloroform, acetone, ether, and the like) and sparingly soluble in aqueous solvents. The term includes, but is not limited to, fatty acids, fatty acid esters such as triglycerides, long chain fatty alcohols and waxes, deoxycholate, sphingoids, glycolipids, phospholipids, sphingolipids, and isoprenoids, such as steroids.

"Fatty acid" refers to aliphatic monocarboxylic acids. Fatty acids are typically predominantly straight chain acids of 4 to about 30 carbon atoms and may be saturated or unsaturated. Branched fatty acids and hydroxy fatty acids are also included in the term.

"Triglyceride" refers to an ester of a fatty acid and glycerol.

"Non-amphipathic", as used to describe lipids, refers to molecules that do not contain both hydrophobic and hydrophilic segments that form bilayers in aqueous solution.

II. Lipophilic Drug Compositions

The present invention provides a method for increasing the lipophilicity (i.e. hydrophobicity) of a drug molecule using two separate approaches that can be utilized separately or together in a complementary manner. The first approach involves covalent attachment of a lipid molecule to a biologically active drug molecule. The second approach comprises encapsulating the drug in a lipid composition. By attaching a lipid molecule to a drug molecule or encapsulating a drug in a lipid, the resulting drug composition becomes more lipophilic, which facilitates transport of the composition in the lymphatic system as opposed to transport only through blood plasma. The observed ability of the lipid-tailed nitrothiazole to reach and kill parasites in the central nervous system of horses afflicted with EPM (as described more fully below) is suggestive of a lymphatic transport, since most drugs have difficulty in crossing the blood brain barrier.

The lymphatic pathways begin as lymphatic capillaries, which are close-ended microscopic tubes forming complex networks. Lymph is essentially tissue fluid that has entered a lymphatic capillary. These capillaries merge with other capillaries to form the lymphatic vessels and in turn become the lymphatic trunks. The thoracic duct is the major lymphatic trunk and is similar to the aorta in structure and function. Blood and lymph are the extra-cellular fluids that transport to, and collect from, tissues and organs. After a fatty meal, at least two thirds of the ingested fat can be recovered in the thoracic duct. The lymph plus tissue fluid constitutes two thirds of the extra-cellular fluid. This added lymphatic volume is almost three times larger than blood volume. Bacteria and viruses enter tissue fluids and are transported as foreign particles through the lymphatic system to the lymph nodes. Foreign particles cannot easily enter the blood capillaries, whereas the lymphatic capillaries are easily adapted to receive them.

Delivery of drug molecules through the lymphatic system provides a number of important benefits. For example, the effect of acute toxicity of many drugs can be eliminated or greatly reduced. The lipid/drug conjugate or mixture is believed to be more acceptable to the body because it is more "food-like". In essence, the presence of the lipid molecule disguises the drug and encourages the body to simply process the compound as it would any lipid molecule ingested in food. Thus, the lipophilic conjugates or mixtures are processed in a manner that contrasts sharply with the manner in which many conventional drug molecules are processed. Many drugs are immediately recognized as foreign matter and subjected to rejection by the biochemical detoxification mechanisms of the patient.

Further, lipophilization of drug molecules increases drug absorption and bioavailability, and slows release of the drug. It is believed that the lipophilic drug compositions of the invention are delivered through the lymphatic tissue fluids to the targeted tissue, rather than passing solely through the liver. The metabolism of many drugs by liver enzymes, such as cytochrome P450, is well known. Phase 1 biotransformation is caused by the cytochrome P450 enzymes and a second biotransformation phase, caused by many of the detoxification mechanisms, adds a hydrophilic group, such as glucuronic acid, sulfate or glutathione, and results in drug inactivation. However, the lipophilic drug compositions of the invention, such as drug/lipid conjugates droplets, are absorbed and transported through the lymphatic system and are believed to remain active longer and exhibit slower release profiles. A lipid-like drug which enters the lymph can remain in circulation much longer than conventional drug molecules, due in part to the large size of the lymphatic system as compared to blood volume. The lipophilized drug may also be deposited into the adipose tissue, where it is stored and released at a slow rate.

In the pharmaceutical industry, there is a general belief that lipophilicity of a drug must be moderate (i.e. not too high or too low). There is a bell-shaped relationship between the absorption rate and the partition coefficient, termed log P, in octanol/water. At low P values (log P<−2) (i.e., polar compounds), the drug molecule cannot penetrate the lipid intestinal membrane. Conversely, at high P values (log P>3), the compound becomes so lipid soluble, that the diffusion through the mucous layer of the intestinal membrane becomes the rate-limiting step in the overall absorption process. The conventional view is that a drug must have a P value of about −1<log P<2 (See Houston, et al., *J. Pharmacol. Exp. Ther.*, 195, 67-92, 1975). Hence, the present invention of attaching a lipid tail to a drug molecule represents a drastic departure from the conventional approach of drug design. The unconventional nature of this technique is particularly apparent when it is noted that nothing in the crowded field of oxazolidinones suggests the type of lipidization of a drug molecule described herein and exemplified in Example 13.

Additionally, attachment of a lipid "tail" to the drug molecule or encapsulation of a drug in a lipid can render the molecule more palatable to the patient. The usefulness of some orally-administered drugs is hampered by difficulty in administering the drug at a sufficient dosage level due to the unpleasant taste of the drug. This can be particularly problematic in veterinary medicine. By incorporating a lipid component into the drug composition, the taste of a drug is better accepted by the patient and oral administration of the drug can be improved.

In a preferred aspect of the invention, both approaches are used in complementary fashion. Thus, in this aspect, a drug molecule is covalently attached to a lipid molecule and then encapsulated within a lipid composition. All of the above-described benefits of drug lipidization can be further enhanced by the complementary use of both lipidization approaches. Further, attaching a lipid molecule to a drug molecule prior to encapsulation improves the chemical compatibility of the drug molecule and the encapsulating lipid components.

A. Covalent Attachment of a Lipid "Tail"

As noted above, in one aspect, the invention provides conjugates of a lipid and a biologically active agent. The lipid and drug molecule are covalently attached through a linkage as illustrated by the general structure given below:

D-L-LIPID wherein D is a drug molecule, L is a linkage moiety, and LIPID is a residue of a lipid. As would be understood, the term "residue" is intended to refer to a portion of a molecule that remains after chemical reaction with another molecule. When a fatty acid is used as the lipid component, the residue of the lipid component would comprise a long-chain alkyl group, such as a C4-C30 alkyl group. It is preferable that the drug/lipid conjugate form a homogeneous drug product that is a well defined and substantially pure drug entity.

The lipid molecule is preferably a non-amphipathic lipid that is solid at room temperature (25° C.), such as triglycerides or C4-C30 fatty acids. When a fatty acid is used, the fatty acid is preferably a C7-C30 fatty acid, more preferably a C10-C30 fatty acid. Thus, it is preferable to use fatty acids having a chain length of at least 7 carbon atoms, more preferably at least about 10 carbon atoms.

In a preferred embodiment, D is a biologically active or pharmacologically active core structure of a known class of active compounds, thus forming a new drug entity that is efficacious, less toxic, and more palatable. By first identifying a biologically active core structure, the lipidized drug entity will exhibit efficacy, while also being as structurally simple as possible for ease of synthesis. The biologically active core structure can be identified by analyzing related known active compound structures of a given type and selecting the common structural features shared by all of the active compound derivatives. In the following three tables, examples of biologically active core structures are illustrated for three classes of drugs: floxins, angiotensin converting enzyme (ACE) inhibitors, and penicillins. The biologically active core structure for floxins is the fluoroquinolone structure. It is the minimum core drug structure that confers the antibiotic activity of floxins (see Table 1). Similarly, for ACE inhibitors, the active core structure is the di-peptide ala-pro structure (see Table 2). An example of synthesis of a lipidized conjugate of an ACE inhibitor is discussed in Example 14. For penicillins, the B lactam and thioazolidine rings form the biologically active core structure (see Table 3).

TABLE 1

Floxins
(core structure = fluoroquinolones)

Ciprofloxicin

Fleroxacin

Ofloxacin

Enrofloxicin

TABLE 2

ACE Inhibitors
(core structure = dipeptide ala-pro)

Captopril

TABLE 2-continued

ACE Inhibitors
(core structure = dipeptide ala-pro)

Enalapril

Lisinopril · 2 H₂O

Imidapril

TABLE 3

Penicillins
(core structure = B-lactam plus thioazolidine rings)

Amoxicillin

Ampicillin

Propicillin

As would be understood in the art, a drug molecule can be covalently attached to a lipid by reacting a terminal reactive group on the lipid molecule with a reactive group on the drug molecule. For example, with regard to the synthesis of the new drug, 2-lauramide-5-nitrothiazole, which is described in greater detail below, the carboxy function of lauric acid is reacted with the amino group of 2-amino-5-nitrothiazole in a condensation reaction to form an amide linkage between the drug molecule and the lipid molecule.

If necessary, either the drug molecule or the lipid component, or both, may be chemically modified to form the reactive groups necessary for conjugation. For instance, lauric acid or other fatty acids can be "activated" to form a reactive species that will react readily with an amino group on a drug molecule to form an amide linker. Examples of such activated derivatives include fatty acid-acyl-halides and active esters of fatty acids, such as N-hydroxysuccimidyl esters. Lipids can also be activated with carbodiimadzole or carbodiimide. Conversely, a substituent of the drug molecule, such as a carboxyl group, can be activated and reacted with a long chain alkylamine, such as a C4-C30 alkylamine. In yet another embodiment, a bifunctional linker, such as bromoacetobromide, can be used to bromoacetylate an alkylamine, which is then reacted with an amino functionality on a drug molecule to form a conjugate having the general structure LIPID-NH—CH₂—CO—NH-DRUG. In all three examples, a peptide linkage is generated that can be cleaved enzymatically by a non-specific endopeptidase.

There are numerous examples of reactive functional groups that can be formed on a lipid molecule or drug molecule for reaction with other molecules. Exemplary functional groups include hydroxyl, active esters (e.g. N-hydroxysuccinimidyl, 1-benzotriazolyl, p-nitrophenyl, or imidazolyl esters), active carbonates (e.g. N-hydroxysuccinimidyl, 1-benzotriazolyl, p-nitrophenyl, or imidazolyl carbonate), acetal, aldehyde, aldehyde hydrates, alkyl or aryl sulfonate, halide, disulfide derivatives such as o-pyridyl disulfidyl, alkenyl, acrylate, methacrylate, acrylamide, active sulfone, amine, hydrazide, thiol, carboxylic acid, isocyanate, isothiocyanate, maleimide, vinylsulfone, dithiopyridine, vinylpyridine, iodoacetamide, epoxide, glyoxals, diones, mesylates, tosylates, or tresylate.

The linkage, L, is any type of linkage resulting from the reaction of a functional group on the lipid and a functional group on the drug molecule, or resulting from reaction of a bifunctional linker with a drug molecule and an alkylamine. Examples of suitable linkages include carboxylic acid esters, phosphoesters, thioesters, ethers, thioethers, imides, amides, sulfonamides, phosphonamides, disulfides, and carbamides. The linkage, L, formed between the drug molecule and the lipid molecule is preferably a hydrolytically stable linkage, such as ethers, thioethers, imides, amides, sulfonamides, phosphonamides, disulfides, and carbamides. The linkage moiety should also be enzymatically cleavable, such as a linkage cleavable by esterase, peptidase, hydrolase and the like. In this manner, the parent drug compound will be released from the lipid tail by interaction with one or more enzymes. Amide and imide linkages are particularly preferred enzymatically cleavable, hydrolytically stable linkages. In some embodiments, hydrolytically degradable linkages, such as certain esters, can also be used.

B. Encapsulation of Drug Within Lipid Component

In another aspect of the invention, drug molecules or drug molecule/lipid conjugates are encapsulated by an inert matrix of one or more lipid components to enhance lipidization of the drug molecule and facilitate lymphatic transport. By encapsulating a drug in a protective hydrophobic environment, product stability is also enhanced. The encapsulating lipid is preferably non-amphipathic, meaning the lipid composition used for encapsulation is substantially free of phospholipids, glycolipids or other amphipathic lipids that form bilayers in solution. The encapsulated drug product of the invention preferably comprises a single phase (e.g., solid or liquid). Preferably, the encapsulated drug product is a dry solid, meaning a solid substantially free of water or other solvents. In one embodiment, the encapsulating lipid composition comprises lipids that are solid at 25° C., such as triglycerides, C4-C30 fatty acids or mixtures thereof. The term "encapsulation" means that the lipid composition is in contact with, and physically surrounds and entraps, a substantial portion of the drug combined therewith such that a substantial portion of the drug is no longer physically exposed to the surrounding environment.

When a lipid/drug conjugate is encapsulated, the encapsulating lipid can be isologous (i.e., the lipid used to form the conjugate is identical in chain length to the lipid used in encapsulation), homologous (i.e., the lipids are similar but differ in chain length), or heterologous (i.e., the conjugating lipid is substantially different from the encapsulating lipid, such as one is unsaturated and the other is saturated or one is a phospholipid and the other is a fatty acid). For example, if a C12 fatty acid is attached to a biologically active agent, then an isologous encapsulating lipid composition would comprise, for example, C12 fatty acids and/or triglycerides comprising C12 alkyl chains. A homologous encapsulating lipid composition would comprise lipid components having alkyl chain lengths, for example, within about 5 carbons atoms of the length of the lipid tail attached to the biologically active agent, preferably within about 3 carbon atoms. It is generally preferable to attach the drug to a lipid that is chemically compatible and structurally similar to the encapsulating lipid components, such that the lipid tail and the encapsulating lipid are isologous or homologous lipid compositions.

The encapsulation method of the invention involves blending of the lipid component with the drug molecule and is both simple and low cost. The rationale behind this approach is grounded in basic biochemical knowledge of fat metabolism. In higher mammals, including humans, the metabolism transport and deposition of fat is a known biochemical transformation. Neutral fats or triglycerides are composed of three long fatty acid chains esterified to the trihydric alcohol of glycerol. Ingested fats are emulsified in the small intestine by bile salts to become micelles or oil droplets that are absorbed away from the intestine lumen by lymphatic capillaries. The relatively large absorbed fat micelles known as chylomicrons pass from the intestine through the lymph into the blood. By encapsulating the drug molecule in a lipid composition, the invention mimics the fat micelles in order to enhance the drug absorption from the intestine milieu.

In a preferred embodiment, drug crystals are emulsified with fatty acids and then encapsulated in triglycerides. A preferred triglyceride composition is Sterotex® NF, a fully hydrogenated cottonseed oil available from Albitec Corp. of Janesville, Wis. Sterotex® NF comprises glycerin esters of C14-C22 fatty acids. In pharmaceutical manufacturing, it is a well-known excipient, usually added as a lubricant during the granulation process in tableting. However, in this application, Sterotex is used as a component of an enteric drug delivery formulation.

Although encapsulation with Sterotex® alone has proven to be effective (see Examples 1-3) for drug delivery through the lymphatic system, improved drug delivery is seen when a fatty acid, such as palmitic acid, is incorporated into the process. Example 4 provides a general process for encapsulating a drug in a triglyceride/fatty acid complex. In general terms, the process comprises high shear blending or mixing of the drug or drug/lipid conjugate with one or more fatty acids, such as C4-C30 fatty acids, in the presence of a solvent, to form an emulsion. While continuing to subject the emulsion to high shear blending or mixing, a triglyceride or mixture of triglycerides, such as Sterotex®, is added to the emulsion and mixed therewith using high shear blending. The mixture is then cooled to form a solid composition and dried. It is important to mix the drug with the lipid components with sufficient mixing intensity to form an emulsion. The high shear mixing or blending can be accomplished using high speed or high pressure mixing equipment or by sonification. Examples of suitable mixing apparatus known in the art include Microfluidizer® processors, blenders, sonicators, homogenizers, as well as other mixing apparatus. The mixing energy generated by the high shear blending results in emulsion formation such that the encapsulating lipids and the encapsulated drug or drug/lipid conjugate coalesce into an ordered, layered structure, as evidenced by the freeze-fracture EM photographs referred to in Example 7.

There are a number of reasons for incorporating fatty acids into the drug/lipid complex. First, fatty acids in fat droplets control fat metabolism by pancreatic lipase. In the normal course of fat metabolism, triglycerides are degraded to diglycerides+fatty acids and diglycerides are degraded to monoglycerides+ more fatty acids and monoglycerides are degraded to fatty acids and glycerol. In the presence of free fatty acids, the lipases are less active towards the triglycerides. If the lipase remain highly active, the crystalline drug can be uncoated by converting triglyceride to glycerol and fatty acids. Fatty acids act as an end-product inhibition of the enzyme lipase and thereby prevent the removal of the lipid coating of the encapsulated drug crystals. Second, some polar drugs are difficult to emulsify with fat, whereas fatty acids possessing a carboxylic moiety can better interact with the drug. Lastly, the 85% bound drug found in Example 2 suggests that the complex with Sterotex® could be further improved.

The solvents and fatty acids used in emulsifying a given drug can be modified to accommodate the chemistry of the drug. For example, ethanol or water can be substituted for methanol used in Example 4. Palmitic acid, exemplified in Example 4, is a C-16 carbon chain fatty acid. Substitutions with shorter or longer carbon chains and even deoxycholic acid have been found to be suitable. Preferably, the fatty acid is a C4-C30 fatty acid. In some embodiments, it is preferred to use a C7-C30 fatty acid, more preferably a C10-C30 fatty acid. Thus, it is preferable to use fatty acids having a chain length of at least 7 carbon atoms, more preferably at least about 10 carbon atoms.

Preferably, the weight ratio of the encapsulating lipid component to the drug in the final composition is about 4:1 to about 0.25:1, preferably about 2:1 to about 0.5:1, more preferably about 1:1. If a combination of triglyceride and fatty acid is used as the encapsulating lipid, the weight ratio of triglyceride to fatty acid is preferably about 4:1 to about 1:4, more preferably about 3:1 to about 1:3, most preferably about 2:1 to about 1:2 or about 1:1.

Prior to degradation in vivo, it is preferable for no more than about 50 weight percent, more preferably no more than about 30 weight percent, and most preferably no more than 10 weight percent, of the bound drug to be physically exposed within the composition. By physically exposed is meant that a portion of the drug molecule is exposed to the environment external to the encapsulating lipid composition.

The most advantageous use of the encapsulated formulation of the invention is in oral medication. Virtually all enteric medications have an unpleasant taste and are often bitter. Sterotex® is odorless and tasteless and therefore can be added to food and is acceptable to recipients.

The encapsulation process of the invention is simple and economical (both Sterotex® and palmitic acid are less than $0.02/g). The encapsulated drug complex is stable and yet biologically available. It is palatable to humans and animals and drug absorption through the gastrointestinal tract is enhanced. It guards against acute drug releases and avoids the toxicity of many potent cytotoxic drugs.

C. The Biologically Active Agent

The biologically active moiety or drug may be any biologically active compound that would benefit from lymphatic delivery and benefit from the advantages of lipophilization described above, such as increased circulation time, reduced toxicity, etc. Virtually any biologically active compound would benefit from the lipid encapsulation/attachment methodology described herein. In particular, the following classes of drugs would-benefit from the present invention: cephalosporins, peptides, ACE inhibitors, antibiotics, anticancer, anti-depressant, antihistamine, anti-psychotic, cardiovascular, gastrointestinal, anti-hypertensive, diuretic, amino acid, nucleotide, nucleoside, vaccine, polysaccharide, protein, tranquilizers, narcotics, anti-arthritic, anti-viral, anti-asthmatic, anti-allergy, and the like.

The drug may be utilized per se or in the form of a pharmaceutically acceptable salt. If used, a salt of the drug compound should be both pharmacologically and pharmaceutically acceptable, but non-pharmaceutically acceptable salts may conveniently be used to prepare the free active compound or pharmaceutically acceptable salts thereof and are not excluded from the scope of this invention. Such pharmacologically and pharmaceutically acceptable salts can be prepared by reaction of the drug with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicyclic, p-toluenesulfonic, tartaric, citric, methanesulphonic, formic, malonic, succinic, naphthalene-2-sulphonic and benzenesulphonic, and the like. Also, pharmaceutically acceptable salts can be prepared as alkaline metal or alkaline earth salts, such as sodium, potassium, or calcium salts of a carboxylic acid group.

III. Exemplary Lipophilic Drug Compositions

A. Lipophilic Nitrothiazole Compositions

Equine protozoal myeloencephalitis (EPM) is caused by the intracellular protozoal organism *Sarcocystis neuron* a infecting the CNS. In clinically affected horses, the protozoans infect neurons and induce an inflammatory response. Clinical signs of neurological disease most commonly result in asymmetric coordination (ataxia) weakness, and/or muscle atrophy. The infection progressively worsens and the untreated animals eventually collapse and die. Up to 60% of the horses in some areas of the country, including the Southeast, have been exposed to *S. neurona*. It is estimated that 10% of exposed horses exhibit neurological signs of EPM.

Nitazoxanide (2 acetolyoxy-N-5 nitro-2-thiazolyl otherwise known as NTZ) is a pharmaceutical composition highly effective against a wide variety of parasites, bacteria and viruses in both animals and humans. In the treatment of EPM, it has been shown to be effective against the causative parasite *S. neurona*. The advantage of this pharmaceutical composition is that it is a wide spectrum antibiotic and its mode of action is cidal rather than static. The disadvantage of the drug is that in the free form it is relatively toxic. It is also not palatable and causes anorexia, depression and diathermia or loose stool in horses. In humans, NTZ has been known to cause gastrointestinal upset in the treatment of cryptosporidial diarrhea. The drug also has some safety issues principally due to nitrothiazole. The very nature of its construct along with the aspirin conjugation further exacerbates the gastrointestinal intolerance and damage. Salicylates cause epithelial cell damage and widen both the intracellular junction spaces and the pores of the epithelial cell (see Kingham et. al. Gut 17:354-359(1976). The drug, like aspirin, is unstable because it is susceptible to moisture degradation from the ester to the deacetylated form. In stability studies, the bulk drug progressively degrades. In addition, the sulfur also oxidizes to sulfone and then to sulfoxide as can be visualized by UV scanning from UV max of 350 nm. It is red-shifted to 354 nm (sulfone) and then 358 nm (sulfoxide). When the drug is heated to more than 50° C. the oxidation is most pronounced. The bulk drug has an expiry of two years. A number of patents discuss 5-nitrothiazole derivatives, including U.S. Pat. Nos. 3,950,351; 4,315,018; 5,856,348; 5,859,038; 5,886,013; 5,935,591; 5,965,590; 5,968,961; 6,020,353; and 6,117,894, all of which are incorporated herein by reference.

The present invention provides a safe and efficacious pharmaceutical composition comprising nitrothiazole for the treatment of opportunistic microbes in both humans and animals. It overcomes many safety issues and especially the stability problem of nitazoxanide. The new drug molecule comprises a lipid molecule, such as a fatty acid, covalently attached to a substituted or unsubstituted 5-nitrothiazole compound or derivative thereof, including 2-benzamido-5-nitrothiazole compounds, wherein the aryl ring of the benzamido group may be substituted or unsubstituted (preferred substituents including hydrogen, acyloxy, such as acetoxy or propionoxy, halogen, and alkoxy). Any of the 5-nitro thiazole compounds disclosed in the patents referenced above can be used in the present invention. The lipid molecule can be attached to any atom of any ring structure in the molecule (e.g., the thiazole ring or the aryl ring of the benzamido group), either directly or through a linkage, such as an amide linkage.

A preferred lipid conjugate of a 5-nitrothiazole compound is shown as Formula I below:

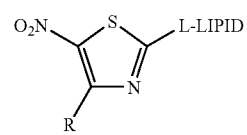

Formula I wherein L is a linkage, such as —NH—C(O)—, R is hydrogen, alkyl, substituted alkyl, aryl, substituted aryl, heteroaryl, substituted heteroaryl, heterocyclic, or substituted heterocyclic, and LIPID is a residue of a lipid, such as a C4-C30 fatty acid. A specific embodiment of a compound of Formula I, 2-lauramide-5-nitrothiazole, is also referred to herein as BA 3540. BA 3540 is chemically synthesized by condensing the carboxyl function of lauric acid to the amino group of 2-amino-5-nitrothiazole (see Example 8). As known to the skilled artisan, activating agents that may be used to form the amide linkage include many activated intermediates of lauryl-acyl-halides, lauryl-active esters such as lauryl-n-hydroxysuccimide ester and also by activation with carbodiimadzole and carbodiimide.

The therapeutic efficacy of the new drug 2-lauramide-5-nitrothiazole is remarkable. The new drug construct must find its way from the intestine to the CNS and it has to possess the cidal activity of NTZ in order to eradicate the parasite. The mechanism of action of the new drug is currently unknown. However, natural multiple thiazole rings peptide antibiotic produced by streptomycetes such as thiostrepton and micrococcin shed light on this issue. The mechanism of action of the antibiotic is due to the binding of the thiazole ring, which inhibits translation and ribosomal GTPase activity. This binding is to a limited and conserved region in the large subunit rRNA found in eubacteria and (plastid) organelles and not to the corresponding region in eukaryotes. Effective treatment of crytosporadium, plasmodium, and toxoplasma by nitrothiazole may also be due to inhibition of plastid-like organelle contained in these parasites. Although not bound by any particular theory, it is reasonable to assume that the new drug 2-lauramide-5-nitrothiazole also functions in the same manner. This discovery in view of the present disclosure has far reaching implications.

NTZ has been proposed for the treatment of a wide variety of parasites, fungi, bacteria and viruses. The new drug 2-lauramide-5-nitrothiazole is equally as effective as NTZ in the treatment of EPM. Thus, it stands to reason that the new drug can be as effective against the same class of opportunistic parasites, fungi, bacteria and viruses. In particular, the nitrothiazole/lipid conjugate of the invention is useful as a treatment of parasitic, bacterial, viral or fungal infection, including infection by nematodes, cestodes, trematodes, and gram + or gram – bacteria, by administering a therapeutically effective amount of the conjugate to the infected mammal (See Examples 9-12). For instance, the nitrothiazole/lipid conjugates of the invention have proven effective against protozoan parasites, such as parasites that cause EPM and coccidiosis, as well as against viruses.

The metabolism of nitazoxanide has been shown to involve deacetylation to tyazoxinide. In view of the present disclosure, the active metabolite cannot be due solely to tyazoxinide. The commonality between the two active drugs is the parent compound 2-amino-5-nitrothiazole. In-vivo, a non-specific endopeptidase can cleave both molecules to 2-amino-5-nitrothioazole. This may offer a hint to the identity of the primary metabolite for both drugs.

In another aspect, the present invention provides nitrothiazole, such as the nitrothiazole derivatives described above (whether conjugated to a lipid or in free form), encapsulated by a lipid composition, such as triglycerides, fatty acids or mixtures thereof, using the methodology described above (see Examples 3 and 6). As noted above and in the appended examples, encapsulating NTZ or other nitrothiazole derivatives in a lipid composition can improve efficacy and bioavailability and reduce toxicity.

B. Lipophilic Ivermectin Compositions

As noted in Examples 5 and 6, ivermectin was encapsulated within a lipid composition and shown to be well tolerated by the patient and effective. The encapsulation method taught herein can also be used with related abamectin, avermectin, moxidectin, and milbemycin compounds.

C. Lipophilic Oxazolidinone Compositions

As noted in Example 13, the lipid attachment and/or encapsulation methodology of the present invention can also be used with 2-oxazolidinones. As shown in the appended example, a 2-oxazolidinone derivative can be covalently attached to a lipid molecule, such as a C4-C30 fatty acid to form a lipophilic derivative. Oxazolidinones are useful as antibacterial agents. Numerous 2-oxazolidinone derivatives are described in U.S. Pat. Nos. 3,931,213; 4,186,129; 5,643,907; 5,565,571; 5,668,286; 5,688,792; 5,700,799; 5,719,154; 6,166,056; 6,288,238; and 6,337,329, as well as EP 0 316 594 A1, all of which are incorporated be reference herein. Any 2-oxazolidinone compound can be encapsulated with a lipid composition and/or covalently attached to a lipid molecule, either directly or through a linkage moiety. For example, any of the oxazolidinones described in the above references could be used in the present invention. Preferably, the 2-oxazolidinone derivatives are substituted at one or more of the atoms of the ring structure, with preferred ring substituents including hydrogen, aryl, substituted aryl, alkyl, substituted alkyl including alkoxy, halogen, $CF_3$, acyl, amino, substituted amino, and $RS(O)_n$—, wherein n is 1-2 and R is alkyl or substituted alkyl. A lipid molecule can be attached to any available atom of the oxazolidinone ring or any atom of any aryl ring attached to the oxazolidinone ring.

In one preferred embodiment, the lipid/oxazolidinone conjugate has the Formula II below:

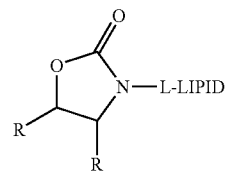

wherein L is a linkage, such as an imide linkage, each R is independently hydrogen, alkyl, substituted alkyl, aryl, substituted aryl, heteroaryl, substituted heteroaryl, heterocyclic, or substituted heterocyclic, and LIPID is a residue of a lipid, such as a C4-C30 fatty acid.

D. Lipophilic Nitroimidazole Compositions

As shown in Example 14, the present invention is also useful in forming lipophilic 5-nitroimidazole compositions. For example, lipid molecules can be covalently attached, either directly or through a linkage, to any available atom in a 5-nitroimidazole ring. In one embodiment, the lipid/drug conjugate as the structure shown below as Formula III:

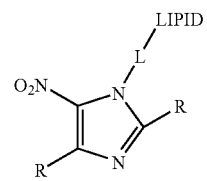

wherein L is a linkage, such as imide, each R is independently hydrogen, alkyl, substituted alkyl, aryl, substituted aryl, heteroaryl, substituted heteroaryl, heterocyclic, or substituted heterocyclic, and LIPID is a residue of a lipid, such as a C4-C30 fatty acid.

IV. Pharmaceutical Composition Comprising the Lipophilic Drug Composition

In another aspect, the invention provides pharmaceutical formulations or compositions, both for veterinary and for human medical use, comprising a lipophilic drug composition as described above comprising a drug covalently attached to, and/or encapsulated within, a lipid.

The pharmaceutical formulation may include one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for-use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), and in "Handbook of Pharmaceutical Excipients", Third Ed., Ed. A. H. Kibbe, Pharmaceutical Press, 2000.

The lipophilic drug compositions of the invention may be formulated in compositions including those suitable for oral, buccal, rectal, topical, nasal, ophthalmic, or parenteral (including intraperitoneal, intravenous, subcutaneous, or intramuscular injection) administration. The lipophilic drug compositions may also be used in formulations suitable for inhalation. Oral administration is a particularly advantageous route of administration for the present invention in light of the increased intestinal absorption and palatability characteristics of the drug compositions of the present invention, as described above. The compositions may conveniently be presented in unit dosage form and may be prepared by any of the methods well known in the art of pharmacy. All methods include the step of bringing the drug composition into association with a carrier that constitutes one or more accessory ingredients. In general, the pharmaceutical compositions are prepared by bringing the drug compositions of the invention into association with a liquid carrier to form a solution or a suspension, or alternatively, bringing the drug composition into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter.

The amount of the biologically active agent or drug in the formulation will vary depending upon the specific drug employed, its molecular weight, and other factors such as dosage form, target patient population, and other considerations, and will generally be readily determined by one skilled in the art. The amount of biologically active agent in the composition will be that amount necessary to deliver a therapeutically effective amount of the drug to a patient in need thereof to achieve at least one of the therapeutic effects associated with the drug. In practice, this will vary widely depending upon the particular drug, its activity, the severity of the condition to be treated, the patient population, the stability of the formulation, and the like. Compositions will generally contain anywhere from about 1% by weight to about 80% by weight drug, typically from about 10% to about 60% by weight drug, and more typically from about 25% to about 50% by weight drug, and will also depend upon the relative amounts of excipients/additives contained in the composition. More specifically, the composition will typically contain at least about one of the following percentages of the drug: 0.5%, 1%, 2%, 3%, 4%, 5%, 6%, 7%, 8%, 9%, 10%, 12%, 14%, 16%, 18%, 20%, 25%, 30%, 35%, 40%, 45% or more by weight.

V. Method of Using the Lipophilic Drug Compositions

As noted above, the lipophilic drug compositions of the invention can be used to improve efficacy, bioavailability, and absorption, as well as reduce toxicity, of a variety of drug molecules. As a result, the compositions of the invention may be used as drug delivery vehicles by entrapping a drug within, or attaching a drug to, a lipid component, such as a triglyceride or fatty acid, and administering a therapeutically effective amount of the resulting composition to a mammal.

The drug compositions of the invention can be used as drug delivery vehicles for any condition responsive to the attached or entrapped drug molecule. Thus, the drug compositions of the invention can be used in pharmaceutical formulations useful for treating any condition responsive to the drug molecule in mammals, including humans. The method of treatment comprises administering to the mammal a therapeutically effective amount of a composition or formulation containing the lipophilic drug composition described above. The therapeutically effective dosage amount of any specific formulation will vary somewhat from drug to drug, patient to patient, and will depend upon factors such as the condition of the patient and the route of delivery. As a general proposition, a dosage from about 0.5 to about 100 mg/kg body weight will have therapeutic efficacy. For example, in certain embodiments, the dosage will be about 10, about 20, about 50, about 75 or about 100 mg/kg. When administered conjointly with other pharmaceutically active agents, even less of the drug composition may be therapeutically effective.

The drug composition may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

VI. Experimantal

The following examples are given to illustrate the invention, but should not be considered in limitation of the invention.

EXAMPLE 1

Encapsulation of Drug in Triglyceride

A general process that can be adapted for direct encapsulation of drug crystals in a triglyceride or mixture thereof, such as Sterotex®, is described in U.S. Pat. No. 6,153,119, which is incorporated herein by reference.

As an example of such a process, 10 g Sterotex® is weighed into a 100 mL screw-cap bottle whereby 30 mL of isooctane or hexane is added and heated to dissolve slowly. The solubilized Sterotex® is maintained at 50° C. An equal weight of drug, 10 g is added to the solubilized Sterotex® and the mixture is shaken vigorously for 5-10 minutes. The resultant mixture is quick cooled in an ice bath while shaking and/or swirling. The cooling mixture will become molten and then slowly solidify. Transfer to a container and dry by pulling vacuum overnight to remove all volatile solvents. The yield is 20 g of 1:1 Sterotex®/drug complex which is usually a white product that can be broken-up into a fine powder. Virtually all pharmaceutical drugs can be emulsified and trapped in this manner.

EXAMPLE 2

Encapsulation of Aspirin in Triglyceride

Aspirin possesses an active ester function and is susceptible to alkaline degradation. In this example, aspirin is encapsulated in Sterotex® using the method described in Example 1. In aspirin, the deacetylated species is salicylic acid, which has a characteristic absorbency at 296 nm. The comparison of drug stability of Sterotex®/aspirin vs. aspirin was made in 0.1 M $NaCO_3$ (10 pH) and the kinetics of degradation monitored by UV spectrophotometry. In FIG. 1, the appearance of salicylic acid is compared between aspirin encapsulated in Sterotex® and free aspirin. Aspirin slowly dissolves and is hydrolyzed to salicylic acid in a basic solution of 0.1 M $NaCO_3$. At 27 hours, it is roughly 38% hydrolyzed. By contrast, aspirin encapsulated in Sterotex® is quite stable even at 27 hours and is only less than 2% degraded. This example illustrates the increase in drug stability provided by encapsulation in a lipid component.

EXAMPLE 3

Encapsulation of Acetylbenzamide Nitrothiazole in Triglyceride

Acetylbenzamide nitrothiazole, otherwise known as NTZ, is an antibiotic drug useful as a treatment for protozoan parasites. Acetylbenzamide nitrothiazole also possesses an active ester function that is susceptible to alkaline degradation to form hydroxybenzamide nitrothiazole with a characteristic absorbency at 360 nm. In water, the parent drug is sparingly soluble and the solution is colorless. Upon standing overnight, the parent drug is converted to the deacetylated counterpart and an intense yellow solution is formed. Acetylbenzamide nitrothiazole encapsulated by Sterotex® as described in Example 1 is hydrophobic and remains afloat on the water surface. A light yellow solution results after many hours at room temperature.

A reasonable estimate of bound versus free drug by UV spectrometry suggests that about 85% of the drug crystals are totally buried in Sterotex®. By increasing the ratio of Sterotex® to drug, this exposed drug percentage does not improve. This higher than expected percentage of free drug suggests that when Sterotex®/nitrothiazole complex is broken-up into fine powder, some drug crystals may be partially exposed and become available to the aqueous milieu. The kinetic of degradation of acetylbenzamide nitrothiazole in 0.1 M $NaCO_3$ is similar to the aspirin curve of FIG. 1. For comparison, the encapsulated drug at 3 hours showed an optical density of 0.1, while the free drug has an optical density of 1.9. This example also illustrates the stabilizing effect of lipid encapsulation.

Sterotex® encapsulates the drug in a hydrophobic environment and it is of utmost importance to show that the drug is bioavailable. The in-vitro bioavailability of acetylbenzamide nitrothiazole in the bound complex was further examined by dissolution testing. The complex versus free nitrothiazole was compared in a Distek® Dissolution Apparatus at 37° C., employing the paddle method (Apparatus I) in 0.1M HCl both with and without a detergent (1% Triton X100). The dissolution of free and Sterotex®-complexed drug (at a ratio of Sterotex®: Drug of: 0.5, 2.0 and 2.5) was first compared at 100 rpm for 120 minutes. Under this condition, all samples show about the same extent of drug release and at the end of dissolution the maximum O.D. was 0.2. When 1% Triton X100 was added to the dissolution media, the drug dissolution was more rapid, although still incomplete. The rate profile of dissolution shows that the Sterotex®/nitrothiazole is about the same as that of the free drug (see FIG. 2).

EXAMPLE 4

Encapsulation of Drug within Fatty Acid and Triglyceride

In the process described below, the drug is first emulsified with high shear blending of a free fatty acid, such as palmitic acid, in a solvent, such as a mixture of methanol and isooctane. The complex formed is coated a second time with Sterotex®. To 125 gm drug, 135 ml of methanol is added in a variable speed Waring blender. The blender is operated 2-3 times at intermediate speed and stopped at intervals to prevent overheating. The total grinding time is 10 minutes at top speed. At this stage, 25 g of palmitic acid (C-16) and 50 ml of isooctane are added. The blender is turned on for ten minutes at intermediate speed. The formation of an emulsion is carefully monitored and more isooctane can be added if the paste is too thick. The blender is then operated at top speed for 30 minutes and again taking care not to allow the temperature to rise above 55° C. When the emulsion thickens, 100 g of melted Sterotex® at about 60° C. is slowly added to the blender while at low speed. Repeat the steps of emulsion grinding at top speed as before. Then the blender is quick cooled in an ice bath. The solidified Sterotex®/palmitic/drug is dried overnight in a vacuum chamber. The final ratio of Sterotex®: palmitic acid is 4:1, and their combined weight ratio to drug remains at ~1:1.

EXAMPLE 5

In-vivo Testing of Sterotex®/Ivermectin and Sterotex®V/Palmitic/Ivermectin

Two oral Sterotex© formulations of the anathematic drug, Ivermectin, was administered to two horses. Conventional formulations consist of either Ivermectin in a paste or in an oil drench that has to be administered by force-feeding. On a monthly basis, horses need to be de-wormed with Ivermectin treatment. The Ivermectin was encapsulated by either formulation, Sterotex®/vermectin and Sterotex®/palmitic/Ivermectin, as described above in Examples 1 and 4. The palatability test was performed by adding 1:1 Sterotex®/drug and Sterotex®: palmitic/drug to a handful of sweet feed consisting of molasses and alfalfa. The time of ingestion was recorded and the horses found either formulation acceptable and consumed both in about the same amount of time as the control sweet feed. The voluntary oral uptake of the drug complex in this and other experiments by horses demonstrate its acceptability as an enteric formulation.

The in-vivo bioavailability was assessed by studying the pharmacokinetic of the drug in individual horses that are treated with either Ivermectin formulation. Blood samples were taken at various times after dosing and plasma were prepared and kept frozen until all samples had been collected.

In FIG. 3, the pharmacokinetic profile is the result of HPLC (high pressure liquid chromatography) analysis by fluorescence of Ivermectin recovered in the blood samples. As shown, the encapsulated formulations exhibited a normal pharmacokinetic profile after a single dose.

EXAMPLE 6

Efficacy of Sterotex®/Ivermectin and Sterotex®/Acetylbenzamide Nitrothiazole in Horses The efficacy of the Sterotex/Ivermectin formulation was assessed by parasite egg count present in the horse feces before and after drug treatment. The egg count before treatment was 350 eggs/L and after treatment it was zero.

The conventional acetylbenzamide nitrothiazole paste is used as a treatment for horses for 6 days at 25 mg/Kg and then at 50 mg/kg body weight daily for a total of 28 treatments. In clinical trials, an encapsulated NTZ formulation (formulated as in Example 4 with both Sterotex® and palmitic acid) was used to treat 4 horses with clinical signs of Equine Protozoal Myeloencephalitis (EPM) at half dose (i.e. 25 mg/Kg) and one horse was treated at one-third dose (i.e., 16.7 mg/kg). The horses infected with neurological protozoan parasites recovered completely after 28 treatments. The treatment with conventional NTZ in other studies remained at 80% efficacy.

The efficacy results indicate that the drug absorption in the gastrointestinal tract is vastly improved by the Sterotex/palmitic encapsulation formulation. It may also be due to the fact that some of the drug may be transported through the lymphatic system and be more effectively delivered through the tissue/body fluids to the targeted neurological organs.

EXAMPLE 7

Freeze Fracture Electron Microscopy Study of the Encapsulated Complex of Sterotex®/Palmitic/Nitrothiazole For freeze-fracture electron microscopy, the samples were quenched using a sandwich technique and liquid nitrogen-cooled propane. The fractured planes were shadowed with platinum for 30 seconds at an angle of 25-35 degrees and with carbon for 35 seconds. The replicas were cleaned with concentrated fuming $HNO_3$ for 24-36 hours. The electron micrographs of FIG. 4 taken at a final magnification of 27,390 show extended areas of layered structures. Presumably, these are ordered lipid layers because in cross-fraction regions, steps of about 4-6 nm are observable. Some structural features that resemble $H_{II}$ lipid phase and the beginning of lipid-tubule-growth are also discernable.

FIG. 5 was taken at 8.3K magnifications. In the final magnification, 1 μm=3.2 cm. In the electron photograph, areas labeled C=Crystal of drug 8×5.7 μm² and CL=crystal layers at 5.6, 18.7 and 57.8 nm of encapsulating lipid. FIG. 6 was taken at about the same magnification and C=crystals at 6×3 μm and 2.8×1.7 μm; CL=crystal layers at 5.8, 19.2, 69.2 nm. This and other electromicrographs show crystals with edge lengths ranging from 0.6 to 8 μm. The actual size of the crystals may be much larger since they have gone through freeze fracture treatment. A large number of CL crystal layers are seen in the EM and in fact, all crystals seem to encompass these thin layers. Taking total measurements at about 200 layers of about 20 cross fraction areas of 4 electronmicrographs, three main thicknesses of crystal layers are seen: ~6 nm being the thinnest, and the rest are ~20 and ~60 nm. There is no certainty as to the upper limit of how thick and wide are these crystal layers.

The freeze fracture EM results illustrate the manner in which the lipid was coated. If it is a random process, the EM will not show repeats in the layering. Since evidence of ordered or structured layers is seen, this suggests that there is an order in which the fatty acids and triglycerides are aligned as the two components are emulsified and allowed to coalesce in the encapsulation process.

EXAMPLE 8

Complementary Drug Lipid-Tail Design for Lipid Encapsulation

The new drug, 2-lauramide-5-nitrothiazole, is also referred herein as BA3540. As described above, it is chemically synthesized by condensing the carboxyl function of lauric acid to the amino group of 2-amino-5-nitrothiazole. As known to the skilled artisan, activating agents that may be used to form the amide linkage include many activated intermediates of lauryl-acyl-halides, lauryl-active esters, such as lauryl-n-hydroxysuccimide ester, and also by activation with carbodiimadzole and carbodiimide. The general reaction scheme is shown in FIG. 7.

In a typical example, an equimolar ratio (approximately 2.5 moles) of lauric acid is activated with dicyclohexyl-carbodiimide (DCC) in 500 mL of dimethylformamide. After 90 minutes, the insoluble dicyclohexylurea formed is removed by vacuum filtration. The activated lauric acid solution is then added in approximately 1:1 ratio of the nucleophile 2-amino-5 nitro-thiazole in 600 mL of methylene chloride, 60 ml of pyridine and made up to 3.5 liters with dimethylformamide. The reaction is allowed to proceed for 40-48 hours with shaking, stirring or heating at 50° C. The product formed is obtained and purified by precipitation and recrystallization in methanol and or acetone. This synthesis scheme is depicted as 2-lauramide-5-nitrothioazole and is a nice needle shaped microcrystal. The bulk drug is oatmeal-colored and insoluble in water, sparingly soluble in methanol and more soluble in methylene chloride and dimethylforamide. To promote complete dissolution, the drug has to be lightly heated. In fact, the new compound is remarkably stable and it can be heated in organic solvents of methanol, acetone, methylene chloride and dimethylforamide at 60-80° C. with no appreciable detriment.

The structural identification was by (1) elemental analysis, (2) UV-spectrum and (3) HPLC. The results of the identification are: C15, H25, N3, O3, Si; 327, Calculated C, 55%, H, 7.6% N, 12.8%, O, 14.7%, S, 9.8% Found 56.25%, 7.5%, 12.8%, (O-not determined) and S, 10.02%. lambda sub-max=350 nm. The UV spectra for BA3540 is shown in FIG. 8. The UV max is dependent on the solvent and is at about 340 nm-350 nm. For the HPLC analysis shown in FIG. 9, the column was C-18 and the mobile phase was in acetonitrile and water. The melting point is 136° C. The lipoidal characteristic of the drug lowered the melting point quite substantially by about 67 degrees as compared to a known aspirin/NTZ conjugate.

Similar synthesis were made with caprylic acid to yield a C-8 adduct and with salicylic acid to yield nitazoxnide (NTZ).

EXAMPLE 9

Efficacy of BA3540 Against EPM in Horses

Approximately 2 kg of the BA3540, 2-lauramide-5-nitrothiazole, were synthesized, purified and crystallized. The new drug was encapsulated as in Example 4 with 27% palmitic acid and 73% of Sterotex®. An illustration of the encapsulated BA3540 product is shown in FIG. 10. The encapsulated drug was made into horse paste formulation as before and tested in three horses that exhibited clinical signs of EPM.

Case 1: "Chris" is a 7 year old quarter horse gelding. The horse had ataxia with lameness of a nonspecific origin, gave only moderate resistance to forefront crossing and was unstable on both sides to lateral tail pull. The horse was also tested and confirmed with immunoblot (Western Blot) to be EPM positive. Chris was given daily oral treatment of the new paste formulation containing lipid encapsulated 2-lauramide-5-nitrothiazole for a total of 28 dosings with 25 gm/syringe. (On day 22 to 28, the drug was not given and then resumed medication in the following week).

On day 9, clinical examination, he stumbled behind when trotted. When standing, he constantly shifted his hind feet, but resisted lateral tail pull. On day 15 examination, Chris shifted hindquarters slightly when standing, but at a trot he stumbled both hind feet. On day 22 examination, Chris resisted lateral tail pull and no longer shifted hindquarters while standing. He appeared to have improved a full grade. By day 30 examination, he stood relaxed on the firm surface, resisted lateral tail pull and had no apparent muscle wasting. Based on general EPM grading, Chris went from Grade 3 to Grade 0/1 by the new drug paste treatment. Owner's observation from day 30 to day 84 indicated that the horse ate well, played in his paddock, and regained an alert and aggressive attitude. Chris had become apparently sound in health.

Case 2: "Brooke" is an 18-year-old thoroughbred mare. The horse had a positive Western Blot serum test for EPM exposure. She had notable right foreleg response and failed to resist crossover for brief periods. Also there was muscle atrophy and edema of the left hindquarter. The right hindquarter failed to resist lateral tail pull. Her EPM syndrome was related to rapid weight loss, especially on the right hindquarter, affecting stifles as well. Other tests (complete blood count and serum enzyme analyses) indicated an elevation in protein globulins at the beginning of drug treatment and a return to normal by the end of the treatment. Again the horse was given daily oral treatments with the current dose of a typical 1000 lb horse at about 50 mg/Kg body weigh or 25 gm/day. The mare maintained good appetite for food throughout the trial.

On day 7 clinical examination, the mare resisted foreleg crossover on both sides yet she yielded to lateral tail pull from both directions. She had slight left hind toe drag after 2-3 minutes lunge, but no stumbling. The left hind leg was swollen from foot to hock. At day 16 examination, muscle loss in the left hindquarter was not as obvious. When lunging clockwise in a circle, she went stiffly and dropped her head for balance. At day 21, her reaction to lateral tail pull had changed; the right hind leg strongly resisted and the left side had only moderate resistance. By day 29, there was strong resistance to foreleg crossover. However on lounge she still dropped her head. On grade scoring she started out at a Grade 2 and remains as grade 2 at that time. From day 29, the mare continued to improve without additional medication. She continued to gain weight, attitude, and aggressiveness. By Day 84, according to the owner, she was running and bucking in her paddock and deemed to be in sound health.

Case 3: "Foundation Man" is a 22-year-old Appaloosa gelding. The horse was examined by three veterinarians who suspected an infection of equine protozoal encephalomyelitis based on clinical signs of stumbling repeatedly on level, familiar ground. The horse had stumbled and fallen with the rider at a trot in his own paddock. The horse had a positive Western blot serum test for EPM exposure. Foundation Man was given daily oral treatments with the same amount of medication for 28 days. The clinical signs of note at weekly examinations were: (1). right lower back muscle spasm and (2). stiffness of motion when lunging clockwise in a circle.

This horse was most responsive to the medication. He maintained an excellent appetite for food throughout the trial. There was a notable improvement in energy, aggressiveness, and vigor by Day 15, which he maintained throughout. Brief stumbles when lunging became less pronounced to none affecting controlled forward motion in either direction. Lower back spasm was also reduced by day 14 and disappeared thereafter. In response to this, his forward motion became more fluid. Based on general characteristics of EPM grading, Foundation Man went from Grade 2/3 to Grade 0 by 28 day of new drug treatment.

As indicated in the testing described above, the lipid conjugate, BA3540 (2-lauramide-5-nitrothiazole) is both efficacious and safe. Unlike NTZ, the drug is palatable and does not cause anorexia, depression, diathermia or loose stool in horses. All three treated horses accepted the formulation with no side effects. Almost all horses gained weight even during the first week of treatment and continued to gain weight during the 28 days treatment. The three treated horses had diverse neurological symptoms and yet all showed progressive improvements during the 28-day treatment period. They continued to improve even after the drug treatment period with no medication or supplements. Reports from the owners indicate that all three horses fully recovered from EPM and i show no relapse at day 84.

EXAMPLE 10

Efficacy of BA 3540 in Treating Coccidiosis in Chickens

An initial trial involving 120 broilers (4 week old chickens) for the treatment of coccidiosis was made. Three treatment groups were used: (1) control, (2) low dose of 10 mg BA 3540/kg treatment, and (3) high dose at 50 mg BA 3540/kg treatment. The broilers were separated into six pens, each with 10 birds. Fecal collection was begun to check for the presence of coccidian. The treatments were then assigned and the trial started. The treatment was added to a mash diet and fed adlib for seven days. At the end of the treatment period, new fecal collections for each treatment group were analyzed for the presence of coccidia.

The drug formulation was accepted by the broilers with no adverse effect and all broilers remained in good health throughout the seven weeks with no mortality. Two fecal samples were taken from each pen and a fecal float was done to check oocyst levels. Oocyst levels are considered to determine the adult coccidian present in an intestinal tract. The level of coccidia infestation at the beginning of the trial was moderate.

After the seven weeks of treatment, the high dose group (50 mg/kg) only had 1 of 4 samples with detectable oocyst. The drug therefore is efficacious in the high treatment group. In the low treatment group (10 mg/kg), the amount of oocyst is about the same as the control group. The oocyte count is not discriminating enough to differentiate between the low treatment group and the control group.

A confirmatory trial was conducted with 10 seven-week-old Arbor Acres broilers. The birds were divided into two groups: control and 50 mg/kg treatment groups. The two set of cages were off the floor to prevent any potential contamination. The trial was monitored for four days and fecal floats for oocyte population were used to determine efficacy. Two fecal samples were collected from each cage. The control fecal samples showed similar levels of coccidial oocytes, while the treatment group showed no visible oocytes.

EXAMPLE 11

Antifungal Activity of BA 3540

The antifungal activity has been demonstrated for NTZ (see U.S. Pat. Nos. 5,578,621 and 3,950,351). These patents suggest that in-vitro yeast and various dematophites are susceptible to nitrothiazole (nitazoxanide). In the present study, patients suffering from yellow fungal toes were treated with a 3% weight percent BA3540 in a gel formulation (gel comprises propylene glycol and 0.8% Carbopol® Gel) for 5 consecutive days by topical application of the gel formulation on the surrounding nail cuticle area, followed by weekly treatment with the gel formulation for the next 4 weeks. The thickening of the nail caused by fungal growth disappeared after two weeks, and several months later a healthy nail began to appear behind the thick nail.

EXAMPLE 12

Antiviral Activity of BA 3540

NTZ has been described as possessing antiviral activity, and specifically against Herpes Virus, such as Epstein Barr virus (EBV), Varicella Zoster virus (VZV), Human Simplex virus (HSV) and Human Cytomalovirus (HCMV). A preliminary assessment of anti-HSV and anti-HCMV activities of BA3540 is made by using NTZ as a positive control.

The drugs, NTZ and BA 3540, were made soluble at 10 mg/mL in dimethylsulfoxide and then diluted in media to 50 µg/mL, 5 µg/mL, 2.5 µg/mL, and 1.5 µg/mL. Human embryonic fibroblast cells were propagated in minimal essential media and supplemented with 10% fetal bovine serum. Cells were pre-treated with the two drugs at the 4 specified concentrations plus a zero control for 45 minutes. The plates were each infected with 300-400 viral particles of either HSV or HCMV for 1 hour. Drug free media was added to each plate and incubation continued for 3 days to propagate virus. At the end of three days, the supernatant from each of the plates was removed for plaque reduction assays.

Both drugs were effective as antiviral agents. This is especially true with respect to HCMV. In controls, there were 300 plaques. BA 3540 at 1.5 µg/mL and 2.5 µg/mL showed 3 and 1 plaques, respectively, and none at the higher drug concentrations. NTZ control showed 310 plaques, whereas there were no viral plaques at all four drug concentrations. The projected therapeutic range for BA 3540 is about 1.5-2.5 µg/mL for HCMV. The therapeutic range of BA 3540 with respect to HSV is about 5-10 µg/mL. In productively infected HSV control there were 110 plaques, whereas at 1.5 µg/mL there were 90 plaques. The present data establishes that BA 3540, like NTZ, is effective as an antiviral agent for Herpes Virus.

EXAMPLE 13

Synthesis of BA 11671, N-dodecyl-2-oxazolidinone (N-lauryl-oxazolidinone)

2-Oxazolidinone is a new class of antibiotic marketed under the trademark, Zyvox®, by Pharmacia Upjohn. It is the first complete new class of commercialized antibiotics in 35 years. Linezolid tablets and injectables are for the treatment of gram-positive bacteria and pneumonia caused by methicillin-resistant *Streptococcus pneumoniae* and *Staphylococcus aureus*. The core structure of oxazolidinone is a five-member ring. The drug derivatives are built around the core nitrogen at position 3 in the oxazolidinone ring. Hence various permutations and combinations of analogs of phenyloxazolidinones have been described (U.S. Pat. No. 6,166,056). Obviously, the phenyl ring is not a prerequisite for activity, because 3-chloro-2-oxazolidinones have been shown to exhibit antibacterial activity (U.S. Pat. No. 3,931,213). However, it is known that the (S)-enantiomer is pharmacologically active. The racemic mixture is useful, but will require twice as much material for the same antibacterial effect. The identification of this core structure constitutes the first step in developing a new drug entity for the lipophilization techniques described herein.

A chemical synthetic approach exemplifies the ease with which a new analog can be generated using the methods described herein. The reaction was an equal molar condensation of laurel chloride and 2-oxazolidinone in dimethylforamide. Pyridine was used to neutralize the HCl generated in the condensation of an imide-bond. After the incubation at 50° C. for 24 hours, the reactants were diluted with two volumes of methanol and crystallized in the cold. The new drug, N-(lauryl)-2-oxazolidinone, was again recrystallized a second time to ensure purity.

The resultant elemental analysis confirmed the composition of the new analog. The structural chemical composition is: C15, H27, N1, O3, with the formula weight of 269. The theoretical composition is: C 67%, N 5.2%, H 10.04%, O 17.76%; found, C 66.96%, N 5.23%, H 10.08%, (O-not determined). The melting point is 69° C. and is significantly lower than that of 2-oxazolidinone (90° C.) because the drug is more lipid-like.

EXAMPLE 14

Synthesis of BA 91346, N-dodecyl-2-methyl-nitroimidazole, (N-(lauryl)-2 methyl-nitroimidazole)

The new drug, BA 91346, is an analog of metronidazole (N-ethanol-2-methyl-5-nitroimidazole). The parent drug is an antibiotic used in the treatment of anaerobic bacteria and in particular for the treatment of ulcer that is caused by the bacteria (*Halobactor.pylori*). It is also used as an anti-parasitic drug.

Chemical synthesis of BA 91346 involved reaction of lauroyl chloride with the imidazole group of 2 methyl-5 nitroimidazole in dimethylforamide and pyridine. Equal molar of the two reactants are mixed and the reaction is for 24 hours at 50° C. The solution was diluted two fold with methanol and chilled to crystallize the compound. After drying, the compound was re-purified by crystallizing from methanol.

The structural formula of the new compound is C 16, N 3, H 28 and O 3; and the formula weight is 310. Elemental analysis theoretical composition of C, 62%, N, 13.5%, H 9.03%, O 15.47%; found C 62.6%, N 13.05%, H 9.08% and O-(not determined). The melting temperature for BA91346 is 74° C. while the parent compound metronidazole is 161° C. Again the observed lower melting temperature is due to lipidization of the drug derivative.

EXAMPLE 15

Synthesis of BA 61274, $CH_3—(CH_2)_{11}—NH—CO—CH_2—S—CH_2—CH(CH_3)—CO$-Pro

The biologically active core structure for Acetocholine Esterase Inhibitor (ACE-Inhibitor) has been described as a dipeptide. In Captopril, there is one mercapto-functionality that can be exploited for linkage to a fatty acid. The simplest approach is to react with lauryol-chloride to yield a thioester. Equal molar of captopril and lauroyl chloride are reacted in dimethylforamide and pyridine for 6 hours at 40° C. Following the reaction, 20 volumes of methanol and three volumes of water are added. The conjugate is precipitated in the cold and recrystallized once more in methanol.

The second approach is to use dodecylbromide and the sulfahydryl of captopril to form a thioether linkage. In this reaction equal molar of the two reactants are added in dimethyformamide and pyridine at room temperature for three days. Following the reaction, methanol and water are added as before and the product is precipitated and recrystallized.

The above two products form either a thioester linkage, which is hydrolysable, or thioether, which is non-enzymatically cleavable. For this reason, a third preferred synthesis option involves the creation of an amide linker that is hydrolytically stable and yet enzymatically cleavable. In the reaction, a bifunctional linker bromoacetyl-bromide is employed. This linker is first attached to the lipid moiety by bromoacetylation. In the reaction, 165 g (1 mole) of n-dodecanoamine is reacted by the slow addition of 222 g (1.1 mole) of bromacetyl-bromide at room temperature for 2 hours in 800 ml of dimethylforamide and 80 mL of pyridine. Following reaction, the precipitated adduct is filtered by vacuum filtration. The product is resuspended in 800 mL of ethylacetate and hexane (1:1) and re-filtered. The product, dodecylamido-acetyl-bromide, has a molecular weight of 306 Da and is crystalline and white. The conjugation reaction is with 1.42 g of dodecylamido-acetyl-bromide and 1 g of captopril in 2 mL of dimethylforamide and 0.25 mL of pyridine for 3 days at room temperature. Following the reaction, 20 volumes of methanol and three volumes of water are added. The conjugate is precipitated in the cold and re-crystallized once more in methanol.

What is claimed:

1. A biologically active lipophilic composition, comprising a substituted or unsubstituted 5-nitrothiazole covalently attached to a lipid, the lipid being selected from the group consisting of fatty acids and esters of fatty acids.

2. The composition of claim 1, wherein the lipid is a C4-C30 fatty acid.

3. The composition of claim 2, wherein the lipid is a C10-C30 fatty acid.

4. The composition of claim 1, wherein the lipid is a fatty acid comprising at least 10 carbon atoms.

5. The composition of claim 1, further comprising one or more pharmaceutically acceptable carriers.

6. The composition of claim 1, wherein the substituted or unsubstituted 5-nitrothiazole covalently attached to a lipid is encapsulated in at least one lipid selected from the group consisting of fatty acids esters of fatty acids, and mixtures thereof.

7. The composition of claim 1, wherein the biologically active lipophilic composition is in solid form and adapted for oral administration.

8. The composition of claim 1, wherein the substituted or unsubstituted 5-nitrothiazole covalently attached to a lipid has the structure:

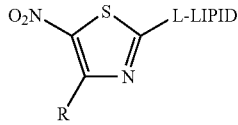

wherein L is a linkage, R is hydrogen, alkyl, substituted alkyl, aryl, substituted aryl, heteroaryl, substituted heteroaryl, heterocyclic, or substituted heterocyclic, and LIPID is a residue of a C4-C30 fatty acid.

9. The composition of claim 8, wherein LIPID is a residue of a C7-C30 fatty acid.

10. The composition of claim 9, wherein LIPID is a residue of a C10-C30 fatty acid.

11. The composition of claim 8, wherein the linkage is hydrolytically stable in aqueous solution at physiologic pH and enzymatically cleavable.

12. The composition of claim 8, wherein L is selected from the group consisting of ethers, thioethers, imides, amides, sulfonamides, phosphonamides, disulfides, and carbamides.

13. The composition of claim 8, wherein L is —NH—C(O)— or —NH—CH2—C(O)—NH—.

14. A biologically active lipophilic composition comprising 2-lauramide-5-nitrothiazole.

15. A method of treating an infection in an animal, comprising administering a therapeutically effective amount of a biologically active lipophilic composition of claim 1.

16. The method of claim 15, wherein said step of administering comprises administering orally.

17. The method of claim 15, wherein the infection is a parasitic, bacterial, viral, or fungal infection.

18. The method of claim 15, wherein the infection is a protozoan infection.

19. The method of claim 15, wherein the infection is equine protozoal myeloencephalitis (EPM) or coccidiosis.

20. The method of claim 15, wherein the animal is selected from the group consisting of humans, horses, and chickens.

21. A method of treating an infection in an animal, comprising administering a therapeutically effective amount of a biologically active lipophilic composition of claim 8.

22. The method of claim 21, wherein said step of administering comprises administering orally.

23. The method of claim 21, wherein the infection is a parasitic, bacterial, viral, or fungal infection.

24. The method of claim 21, wherein the infection is a protozoan infection.

25. The method of claim 21, wherein the infection is equine protozoal myeloencephalitis (EPM) or coccidiosis.

26. The method of claim 21, wherein the animal is selected from the group consisting of humans, horses, and chickens.

27. A method of treating an infection in an animal, comprising administering a therapeutically effective amount of a biologically active lipophilic composition of claim 14.

28. The method of claim 27, wherein said step of administering comprises administering orally.

29. The method of claim 27, wherein the infection is a parasitic, bacterial, viral, or fungal infection.

30. The method of claim 27, wherein the infection is a protozoan infection.

31. The method of claim 27, wherein the infection is equine protozoal myeloencephalitis (EPM) or coccidiosis.

32. The method of claim 27, wherein the animal is selected from the group consisting of humans, horses, and chickens.

* * * * *